United States Patent
Stock et al.

(10) Patent No.: US 8,097,631 B2
(45) Date of Patent: Jan. 17, 2012

(54) FUNGICIDAL COMPOSITION COMPRISING CYPRODINIL

(75) Inventors: David Stock, Bracknell (GB); Adrian Alberto Friedman, Muenchwilen (CH); John Silverthorne, Bracknell (GB); Sarah Barnett, Bracknell (GB); Birgit Forster, Basel (CH); Frederique Guyon, Muenchwilen (CH); Rene Rolf Bircher, Muenchwilen (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 963 days.

(21) Appl. No.: 12/088,279

(22) PCT Filed: Sep. 27, 2006

(86) PCT No.: PCT/EP2006/009405
§ 371 (c)(1),
(2), (4) Date: Mar. 27, 2008

(87) PCT Pub. No.: WO2007/039215
PCT Pub. Date: Apr. 12, 2007

(65) Prior Publication Data
US 2009/0030022 A1    Jan. 29, 2009

(30) Foreign Application Priority Data
Sep. 29, 2005 (EP) ................................ 05021237

(51) Int. Cl.
*A01N 43/54* (2006.01)
*A01P 3/00* (2006.01)

(52) U.S. Cl. ..................................... 514/272

(58) Field of Classification Search .................. None
See application file for complete search history.

(56) References Cited

U.S. PATENT DOCUMENTS

| | | | | |
|---|---|---|---|---|
| 6,566,308 B1* | 5/2003 | Aven | .................... | 504/347 |
| 2005/0197251 A1* | 9/2005 | Ding et al. | ............... | 504/100 |

FOREIGN PATENT DOCUMENTS

| | | |
|---|---|---|
| EP | 0451878 | 1/1986 |
| EP | 0310550 | 9/1988 |
| EP | 0310550 | 4/1989 |
| EP | 0353191 | 7/1989 |
| EP | 0367474 | 10/1989 |
| EP | 0374753 | 12/1989 |
| EP | 0392225 | 3/1990 |
| EP | 0401979 | 5/1990 |
| EP | 0427529 | 11/1990 |
| WO | 9013651 | 11/1990 |
| WO | 9307278 | 4/1993 |
| WO | 9533818 | 12/1995 |
| WO | 9534656 | 12/1995 |
| WO | 9741727 | 11/1997 |
| WO | 03000906 | 1/2003 |
| WO | 03052073 | 6/2003 |

OTHER PUBLICATIONS

"Adjuvant" definition provided from Stedman's Medical Dictionary, 28th edition.*

* cited by examiner

*Primary Examiner* — Shanon A Foley
(74) *Attorney, Agent, or Firm* — Rebecca Howard

(57) ABSTRACT

A fungicidal composition in the form of a liquid concentrate, which, in addition to at least one formulation adjuvant, comprises cyprodinil and an unsaturated $C_{18}$-fatty acid selected from oleic acid, linoleic acid and linolenic acid.

21 Claims, No Drawings

FUNGICIDAL COMPOSITION COMPRISING CYPRODINIL

This application is a 371 of International Application No. PCT/EP2006/009405 filed Sep. 27, 2006, which claims priority to EP 05021237.2 filed Sep. 29, 2005, the contents of which are incorporated herein by reference.

The present invention relates to fungicidal compositions in the form of liquid concentrates, which comprise cyprodinil and an unsaturated $C_{18}$-fatty acid, to processes for their preparation, to mixtures used to prepare those compositions, to aqueous spray mixtures which comprise these compositions and to the use of said compositions for controlling diseases on useful plants caused by phytopathogens.

EP-0-310-550 discloses Cyprodinil ((4-cyclopropyl-6-methyl-pyrimidin-2-yl)-phenyl-amine), a fungicide which is effective against a number of diseases caused by ascomycetes or deuteromycetes. Solid and liquid formulations of cyprodinil are used in the field of crop protection for diverse applications, such as foliar application and seed treatment. Solid formulations of cyprodinil have the unfavourable property of dusting during handling. An advantage of liquid formulations is that these formulations are not dusty.

An example of a liquid formulation for foliar application is a commercially available emulsifiable concentrate (EC) which is sold by Syngenta AG as "STEREO"® fungicide, which comprises 25.0% (w/v) cyprodinil together with 6.25% (w/v) propiconazole and is a substantially water-free emulsifiable concentrate.

An example of a liquid formulation for seed treatment is a commercially available flowable concentrate for seed treatment (FS), which is sold by Syngenta AG as "SOLITAER 060"® fungicide, which comprises 2.5% (w/v) cyprodinil together with 2.5% (w/v) Fludioxonil and 1% (w/v) Tebuconazole and is an aqueous suspension concentrate.

Formulations with high concentrations of active ingredients, the so-called "concentrate" formulations, are interesting to the agrochemical industry as these reduce significantly production, transport and storage costs. However, liquid formulations of cyprodinil with high concentrations of cyprodinil usually show only a limited storage stability.

In seed treatment, aqueous concentrate formulations are commonly used. Cyprodinil is a substantially water-insoluble compound. Out of this reason, compared to substantially water-free concentrate formulations lower concentrations of cyprodinil, such as 2% (w/v) cyprodinil, are commonly used for seed treatment formulations. Also seed treatment formulations of cyprodinil usually show only a limited storage stability.

There is therefore proposed in accordance with the present invention a fungicidal composition in the form of a liquid concentrate, which, in addition to at least one formulation adjuvant, comprises cyprodinil and an unsaturated $C_{18}$-fatty acid selected from oleic acid, linoleic acid and linolenic acid.

It has now been found, surprisingly, that the compositions according to the invention have an increased storage stability compared with cyprodinil comprising liquid compositions that do not comprise an unsaturated $C_{18}$-fatty acid selected from oleic acid, linoleic acid and linolenic acid.

This increased storage-stability leads to a number of benefits. One benefit is the reduced production, packaging, transport and storage cost per unit weight of cyprodinil as a result of minimizing the amount of carrier and/or solvent included in the composition. Another benefit is the reduction in the amount of packaging materials that the end-user has to dispose of. Yet another benefit is the added convenience to the end-user of handling fewer packages to treat a given area of land. Out of these reasons even a small increase in the amount of cyprodinil per total volume of formulation is associated with a considerable benefit.

However, besides the increased storage stability, the composition according to the invention can have also further surprising advantageous properties. Examples of such advantageous properties that may be mentioned are: advantageous behaviour during formulation and/or upon application, for example upon emulsifying or tank-mixing with other products; it lowers the rate of application of cyprodinil whilst the action remains equally good, it still achieves sufficient phytopathogen control even where the control by cyprodinil would be not sufficient for agricultural uses in such a low application rate range.

Other examples of such advantageous properties that may be mentioned are improved characteristics of the useful plants including: crop yields, less dead basal leaves, stronger tillers, greener leaf color, less fertilizers needed, less seeds needed, less plant verse (lodging) and/or improved plant vigor.

According to the instant invention Cyprodinil can be used to prepare the compositions of the invention either in the free form or as a salt or metal complex thereof.

Of the acids that can be used for the preparation of salts of cyprodinil, the following may be mentioned: hydrohalic acids, such as hydrofluoric acid, hydrochloric acid, hydrobromic acid or hydriodic acid; sulfuric acid, phosphoric acid, nitric acid, and organic acids, such as acetic acid, trifluoroacetic acid, trichloroacetic acid, propionic acid, glycolic acid, thiocyanic acid, lactic acid, succinic acid, citric acid, benzoic acid, cinnamic acid, oxalic acid, formic acid, benzenesulfonic acid, p-toluenesulfonic acid, methanesulfonic acid, salicylic acid, p-aminosalicylic acid, 2-phenoxybenzoic acid, 2-acetoxybenzoic acid and 1,2-naphthalene-disulfonic acid.

Metal complexes consist of the underlying organic molecule and an inorganic or organic metal salt, for example a halide, nitrate, sulfate, phosphate, acetate, trifluoroacetate, trichloroacetate, propionate, tartrate, sulfonate, salicylate, benzoate, etc., of an element of main group II, such as calcium and magnesium, and of main groups III and IV, such as aluminium, tin or lead, and of subgroups I to VIII, such as chromium, manganese, iron, cobalt, nickel, copper, zinc, etc. Preference is given to the subgroup elements of the 4th period. The metals may have any of the different valences in which they occur. The metal complexes can be mono- or poly-nuclear, i.e. they can contain one or more organic molecule components as ligands.

In one embodiment of the invention, cyprodinil is used in the free form to prepare the combinations of the invention.

The term "$C_{18}$-fatty acid" according to the invention means a fatty acid with 18 carbon atoms. Examples for unsaturated $C_{18}$-fatty acids are oleic acid, linoleic acid and linolenic acid.

Preferably, the compositions according to the invention comprise oleic acid. An advantage of this embodiment of the invention is that oleic acid is less expensive than linoleic acid or linolenic acid.

According to the invention the term "liquid composition" denotes a composition, which comprises one or more liquid phases and may comprise additionally one or more non-liquid-phases, such as solid phases, the predominant phase by weight in such compositions being a liquid phase. Such a liquid composition comprising cyprodinil can be, for example, but is not limited to, an emulsifiable concentrate (EC), a suspo-emulsion (SE), an oil-in-water-emulsion (EW), a dispersible concentrate (DC), a micro-emulsion (ME), a capsule suspension (CS), an emulsion for seed treatment (ES), a flowable concentrate for seed treatment (FS), a solution for seed treatment (LS) or a capsule suspension for seed treatment (CF).

According to the invention the term "concentrate composition comprising cyprodinil" means a composition, which comprises a high concentration of cyprodinil. The exact value of the concentration of cyprodinil depends on the chemical characteristics of the composition and is mainly dependent on the solvent chosen. The concentration is as high as possible, but it is limited by the storage stability of the composition. Compositions with a maximal concentration of cyprodinil have less than optimal storage stability characteristics. A substantially water-free composition with an optimal solvent for cyprodinil usually has a much higher concentration of cyprodinil compared to aqueous compositions.

Such "concentrate compositions comprising cyprodinil" are usually sold as commercial products to the end-users.

Typically, the end-user will employ diluted formulations. Such "diluted formulations", e.g. typical application-forms of the formulation according to the invention, may, for example, contain from 0.01 to 20% by weight, preferably from 0.01 to 5% by weight of cyprodinil. Typically, the end user will dilute the commercial product with water before the application to useful crops or to plant propagation material thereof.

In one embodiment of the invention the liquid concentrate composition is substantially water-free. Preferably, "substantially water-free" means less then 2% (w/v) water in the total composition, more preferably less then 1% (w/v) water, even more preferably less then 0.5% (w/v) water. Examples for typically substantially water-free liquid concentrate compositions are emulsifiable concentrates or dispersible concentrates.

In a preferred embodiment of said embodiment of the invention, the substantially water-free liquid concentrate composition comprise at least 26% (w/v) cyprodinil, more preferably at least 30% (w/v) cyprodinil.

In a preferred embodiment of said embodiment of the invention, the substantially water-free liquid concentrate composition comprise from 27% (w/v) to 53% (w/v) cyprodinil, more preferably from 29% (w/v) to 39% (w/v) cyprodinil, even more preferably from 29% (w/v) to 37% (w/v) cyprodinil, most preferably from 30% (w/v) to 35% (w/v) cyprodinil.

In another embodiment of the invention, the liquid concentrate composition is an aqueous composition. Examples for typically aqueous concentrate compositions are suspo-emulsions, oil-in-water-emulsions, micro-emulsions, capsule suspensions, emulsions for seed treatment, flowable concentrates for seed treatment, solutions for seed treatment or capsule suspensions for seed treatment.

In a preferred embodiment of said embodiment of the invention, the aqueous concentrate composition comprise at least 1% (w/v) cyprodinil, more preferably at least 2% (w/v) cyprodinil.

In a preferred embodiment of said embodiment of the invention, the aqueous concentrate composition comprise from 1% (w/v) to 10% (w/v) cyprodinil, more preferably from 1% (w/v) to 5% (w/v) cyprodinil; preferred composition falling under this embodiment of the invention are emulsions for seed treatment, flowable concentrates for seed treatment, solutions for seed treatment or capsule suspensions for seed treatment.

In another preferred embodiment of said embodiment of the invention, the aqueous concentrate composition comprise from 5% (w/v) to 37% (w/v) cyprodinil, more preferably from 25% (w/v) to 37% (w/v) cyprodinil; preferred composition falling under this embodiment of the invention are suspo-emulsions, oil-in-water-emulsions, micro-emulsions, capsule suspensions; more preferably suspo-emulsions, oil-in-water-emulsions or micro-emulsions; most preferably oil-in-water-emulsions.

In another preferred embodiment of said embodiment of the invention, the aqueous concentrate composition comprise from 1% (w/v) to 10% (w/v) cyprodinil, more preferably from 5% (w/v) to 10% (w/v) cyprodinil; a preferred composition falling under this embodiment of the invention is a capsule suspension.

The term "storage stability" as applied to a "liquid composition" means that the liquid composition does not deteriorate for at least one month within a range of temperatures, which include extreme temperatures that can be experienced under normal storage conditions, for example a range from 0° C. to 40° C. or preferably a range from −10° C. to 54° C.

The term "deteriorate" as applied to a "liquid composition" means that the "characteristics of relevance to the end-user" of the undiluted composition or of the composition diluted in water—to give concentrations likely to be applied by the end-user—do not worsen during the above mentioned storage conditions.

"Characteristics of relevance to the end-user" are characteristics related to the intended use. Said intended use can be, but is not limited to the use of the composition diluted in water. Examples of such relevant characteristics are: minimal or no crystal growth in the liquid composition during storage time; minimal or no crystal growth on dilution in water; complete redispersion of any non-emulsified residue after dilution in water and/or small uniform emulsion droplets on dilution in water.

The term "storage stability" as applied to a "liquid composition" means preferably that the predominant liquid phase of the liquid composition does not phase-separate and/or does not show crystal development, for at least one month within a range of temperatures likely to be experienced in normal storage, for example a range from 0° C. to 40° C.

Preferably the composition does not phase-separate, without crystal development over a wider temperature range, for example from −10° C. to 54° C. More preferably the composition does not phase-separate, without crystal development over a temperature range of −10° C. to 50° C. for at least 2 weeks.

According to the invention "crystal development" means non-acceptable crystal growth under commercial considerations, such as any crystal growth that may reduce the ease of handling of the composition by the user. Examples of such non-acceptable crystal growth are the development of crystals within the composition, or when the composition is diluted in water, that may cause nozzle or filter blockage during application by the end-user Preferably, the unsaturated $C_{18}$-fatty acid is present in the composition in a weight ratio of cyprodinil to the unsaturated $C_{18}$-fatty acid from 20:80 to 80:20.

Further preferably, the unsaturated $C_{18}$-fatty acid is present in the composition in a weight ratio of cyprodinil to the unsaturated $C_{18}$-fatty acid from 30:70 to 70:30.

Further preferably, the unsaturated $C_{18}$-fatty acid is present in the composition in a weight ratio of cyprodinil to the unsaturated $C_{18}$-fatty acid from 40:60 to 60:40.

Further preferably, the unsaturated $C_{18}$-fatty acid is present in the composition in a weight ratio of cyprodinil to the unsaturated $C_{18}$-fatty acid from 40:60 to 50:50.

Further preferably, the unsaturated $C_{18}$-fatty acid is present in the composition in a weight ratio of cyprodinil to the unsaturated $C_{18}$-fatty acid of about 44:56.

The term "formulation adjuvant" according to the invention denotes a natural or synthetic, organic or inorganic material with which cyprodinil is combined in order to facilitate its application to the plant, to the plant propagation material or to the soil. This adjuvant is hence generally inert, and it must be agriculturally acceptable, in particular to the plant or plant propagation material being treated.

The formulation adjuvant can be a carrier or a surfactant. In compositions according to the invention more than one adjuvant can be present, in such embodiments more than one carrier and/or more than one surfactant can be present, a non-limiting example would be one carrier and two surfactants.

The "carrier" can be a liquid carrier (water, alcohols, ketones, petroleum fractions, aromatic or paraffinic hydrocarbons, chlorinated hydrocarbons, liquefied gases, and the like) or a solid carrier.

Suitable liquid carriers are, but are not restricted to: aromatic hydrocarbons, in particular the fractions $C_8$ to $C_{12}$, such as xylene mixtures or substituted naphthalenes, phthalic esters such as dibutyl or dioctyl phthalate, dipropylene glycol dibenzoate, aliphatic hydrocarbons such as cyclohexane or paraffins, alcohols and glycols as well as their ethers, esters and diesters, such as ethylene glycol monomethyl ether, ketones such as cyclohexanone, strongly polar solvents such as, but not restricted to, N-methyl-2-pyrrolidone, dimethyl sulfoxide or dimethylformamide, and, if appropriate, epoxidized vegetable oils or soybean oil; or water.

Suitable solid carriers are, but are not restricted to: aluminium silicate, urea, sodium sulphate, talc, calcium sulphate or potassium sulphate.

According to the invention a single carrier or a mixture of two or more carriers may be present in the composition according to the invention.

Preferred carriers are liquid carriers.

Preferred carriers are di-propyleneglycol dibenzoate, benzyl benzoate, acetophenone, benzyl acetate, decanol, n-octyl pyrrolidone, dodecane, glycerol triacetate, methyl benzoate, octanol, methyl oleate ("Agnique ME 181-G"®) and 2-ethylhexyl benzoate ("Prifer 6813"®).

The compositions according to the invention include from 0 to 69% (w/v) of a carrier, preferably from 10 to 50% (w/v), more preferably from 15 to 35% (w/v), most preferably from 10 to 25% (w/v).

"Surfactants" are non-ionic, cationic, amphoteric and/or anionic surfactants having good emulsifying, dispersing and wetting properties. According to the invention a single surfactant or a mixture of two or more surfactants may be present. The surfactants customarily employed in formulation technology are described, inter alia, in the following publications: "McCutcheon's Detergents and Emulsifiers Annual", MC Publishing Corp., Glen Rock, N.J., 1988 and M. and J. Ash, "Encyclopedia of Surfactants", Vol. I-III, Chemical Publishing Co., New York, 1980-1981.

Among the surfactants there may be mentioned, e.g., polyacrylic acid salts, lignosulphonic acid salts, phenolsulphonic or (mono- or di-alkyl)naphthalenesulphonic acid salts, laurylsulfate salts, polycondensates of ethylene oxide with lignosulphonic acid salts, polycondensates of ethylene oxide with fatty alcohols or with fatty acids or with fatty amines, substituted phenols (in particular alkylphenols or arylphenols such as mono- and di-(polyoxyalkylene alkylphenol) phosphates, polyoxyalkylene alkylphenol carboxylates or polyoxyalkylene alkylphenol sulfates), salts of sulphosuccinic acid esters, taurine derivatives (in particular alkyltaurides), polycondensates of ethylene oxide with phosphated tristyrylphenols and polycondensates of ethylene oxide with phosphoric esters of alcohols or phenols.

Preferably at least one surfactant is present to improve the formulation characteristics as cyprodinil, the unsaturated $C_{18}$-fatty acid and possibly the carrier are not soluble in water and the end-user will apply the compositions according to the invention typically after dilution with water.

The compositions according to the invention typically include from 0 to 69% (w/v) of a agriculturally acceptable surfactant or of a mixture of agriculturally acceptable surfactants, preferably from 0 to 20% (w/v), more preferably from 5 to 15% (w/v).

Compositions according to the invention may comprise one or more further agrochemical active ingredients, such as herbicides, fungicides, insecticides, nematocides, acaricides, bactericides, molluscicides, rodenticides and/or plant-growth regulators.

Liquid concentrate compositions comprising cyprodinil are, for example, an emulsifiable concentrate (EC), an oil-in-water-emulsion (EW), a suspo-emulsion (SE), a dispersible concentrate (DC), a micro emulsion (ME), a capsule suspension (CS), an emulsion for seed treatment (ES), a flowable concentrate for seed treatment (FS), a solution for seed treatment (LS) and a capsule suspension for seed treatment (CF). An EC formulation is a solution of one or more active ingredients in at least one water immiscible solvent, and containing one or more emulsifiers such that on dilution in water a stable emulsion is formed before application to the target crop.

In the case that the composition according to the invention is a suspo-emulsion, cyprodinil is dissolved in the liquid phase and one or more further agrochemical active ingredients are in suspended form, an example for such a composition is a composition comprising cyprodinil, fludioxonil and flutriafol. In said composition cyprodinil is dissolved in the liquid phase and fludioxonil and flutriafol are in suspended form.

In one embodiment of the invention, compositions according to the invention are emulsifiable concentrates.

In another embodiment of the invention, compositions according to the invention are emulsions.

In another embodiment of the invention, compositions according to the invention are suspo-emulsions.

Within that embodiment of the invention, the suspo-emulsions are preferably aqueous suspo-emulsions.

Whereas the commercial products (compositions according to the invention) will be formulated as "concentrates" comprising a high concentration of cyprodinil, the end-user will typically employ diluted formulations. Such "diluted formulations", e.g. typical application-forms of the formulation according to the invention, may, for example, contain from 0.01 to 20% by weight, preferably from 0.01 to 5% by weight of cyprodinil. Typically, the end user will dilute the commercial product with water before the application to useful crops or to plant propagation material thereof.

An example for such a "diluted formulations" is an aqueous spray mixture for foliar application.

Therefore the invention further relates to an aqueous spray mixture that, in addition to at least one formulation adjuvant, comprises cyprodinil and the unsaturated $C_{18}$-fatty acid.

Said compositions according to the invention may be produced in conventional manner, e.g. by mixing cyprodinil, the unsaturated $C_{18}$-fatty acid and optionally other active ingredients with appropriate formulation adjuvants (carriers, diluents, solvents, fillers and optionally other formulating ingredients such as surfactants, biocides, anti-freeze, stickers, thickeners and compounds that provide adjuvancy effects).

Typically, the mixture obtained by combining cyprodinil with the unsaturated $C_{18}$-fatty acid is a liquid at ambient temperature. This provides formulation advantages compared with the free cyprodinil, which is a solid at ambient temperature.

The invention further relates to a process for the preparation of a composition according to the invention, which comprises mixing cyprodinil with the unsaturated $C_{18}$-fatty acid and with at least one formulation adjuvant.

When carrying out said process for the preparation of a composition according to the invention, cyprodinil can be mixed with the unsaturated $C_{18}$-fatty acid and with at least one formulation adjuvant in any order of mixing partners.

A preferred way to produce the compositions according to the invention is to first produce a mixture consisting of cyprodinil and the unsaturated $C_{18}$-fatty acid. Mixtures consisting of cyprodinil and the unsaturated $C_{18}$-fatty acid are new and were especially prepared for the invention. Accordingly, they also form part of the subject-matter of the present invention.

Preferably, the unsaturated $C_{18}$-fatty acid is present in the mixture in a weight ratio of cyprodinil to the unsaturated $C_{18}$-fatty acid from 20:80 to 53:47.

Further preferably, the unsaturated $C_{18}$-fatty acid is present in the mixture in a weight ratio of cyprodinil to the unsaturated $C_{18}$-fatty acid from 30:70 to 53:47.

Further preferably, the unsaturated $C_{18}$-fatty acid is present in the mixture in a weight ratio of cyprodinil to the unsaturated $C_{18}$-fatty acid from 40:60 to 53:47.

Further preferably, the unsaturated $C_{18}$-fatty acid is present in the mixture in a weight ratio of cyprodinil to the unsaturated $C_{18}$-fatty acid of about 44:56.

The composition according to the invention is effective against harmful microorganisms, such as microorganisms, that cause phytopathogenic diseases on useful plants, in particular against phytopathogenic fungi and bacteria. The composition according to the invention is effective especially against phytopathogenic fungi belonging to the following classes: Ascomycetes (e.g. *Venturia, Podosphaera, Erysiphe, Monilinia, Mycosphaerella, Uncinula, Botrytis, Helminthosporium, Rhynchosporium, Fusarium, Septoria, Cercospora, Pyricularia* and *Pseudocercosporella herpotrichoides*); Basidiomycetes (e.g. the genus *Hemileia, Rhizoctonia, Phakopsora, Puccinia, Tilletia*); *Fungi imperfecti* (also known as Deuteromycetes; e.g., *Alternaria*).

According to the invention "useful plants" typically comprise the following species of plants: cereals, such as wheat, barley, rye or oats; beet, such as sugar beet or fodder beet; fruits, such as pomes, stone fruits or soft fruits, for example apples, pears, plums, peaches, almonds, cherries, strawberries, raspberries or blackberries; leguminous plants, such as leans, lentils, peas or soybeans; oil plants, such as rape, mustard, poppy, olives, sunflowers, coconut, castor oil plants, cocoa beans or groundnuts; cucumber plants, such as marrows, cucumbers or melons; fibre plants, such as cotton, flax, hemp or jute; citrus fruit, such as oranges, lemons, grapefruit or mandarins; vegetables, such as spinach, lettuce, asparagus, cabbages, carrots, onions, tomatoes, potatoes, cucurbits or paprika; lauraceae, such as avocados, cinnamon or camphor; maize; tobacco; nuts; coffee; sugar cane; tea; vines; hops; durian; bananas; natural rubber plants; turf or ornamentals, such as flowers, shrubs, broad-leaved trees or evergreens, for example conifers. This list does not represent any limitation.

The term "useful plant" is to be understood as including also useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors) as a result of conventional methods of breeding or genetic engineering. To give a general example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady® and LibertyLink®.

The term "useful plants" is to be understood as including also useful plants which have been so transformed by the use of recombinant DNA techniques that they are capable of synthesising one or more selectively acting toxins, such as are known, for example, from toxin-producing bacteria, especially those of the genus *Bacillus*. Toxins that can be expressed by such transgenic plants include, for example, insecticidal proteins, for example insecticidal proteins from *Bacillus cereus* or *Bacillus popliae*; or insecticidal proteins from *Bacillus thuringiensis*, such as δ-endotoxins, e.g. CryIA (b), CryIA(c), CryIF, CryIF(a2), CryIIA(b), CryIIIA, CryIIIB (b1) or Cry9c, or vegetative insecticidal proteins (VIP), e.g. VIP1, VIP2, VIP3 or VIP3A.

The term "useful plants" is to be understood as including also useful plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above. Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defense (so-called "plant disease resistance genes", as described in WO 03/000906).

The term "locus" of a useful plant as used herein is intended to embrace the place on which the useful plants are growing, where the seeds of the useful plants are sown or where the seeds of the useful plants will be sown. An example for such a locus is a field, on which useful plants are growing.

The invention further relates to a method of controlling diseases on useful plants caused by phytopathogens, which comprises applying to the useful plants, propagation material thereof or to the locus thereof a composition according to the invention or an aqueous spray mixture comprising the composition according to the invention.

In one embodiment of the invention, the composition according to the invention is co-applied together with one or more further agrochemical active ingredients, such as herbicides, fungicides, insecticides, nematocides, acaricides, bactericides, molluscicides, rodenticides and/or plant-growth regulators.

In another embodiment, the composition according to the invention is co-applied together with at least one fungicide selected from Azoxystrobin, Boscalid, Chlorothalonil, Cyflufenamid, Cyproconazole, Difenoconazole, Dimoxystrobin, Epoxiconazole, Fenpropidin, Fenpropimorph, Fludioxonil, Folpet, Flusilazol, Fluoxastrobin, Ipconazole, Mancozeb, Metconazole, Metrafenone, Penconazole, Penthiopyrad, Picoxystrobin, Prochloraz, Propiconazole, Proquinazid, Prothioconazole, Pyraclostrobin, Pyribencarb, Quinoxyfen, Spiroxamine, Tebuconazole, Trifloxystrobin, Benalaxyl, Benalaxyl-M, Bitertanol, Carboxin, Carpropamid, Copper, Cyazofamid, Cymoxanil, Famoxadone, Fenamidone, Fenhexamide, Fenpiclonil, Fluazinam, Fluquinconazole, Fluoxastrobin, Flutolanil, Flutriafol, Guazatine, Hexaconazole, Hymexazole, Imazalil, Iprodione, Metalaxyl, Mefenoxam, Nuarimol, Oxpoconazole, Paclobutrazol, Pencycuron, Procymidone, Pyrimethanil, Pyroquilon, Silthiofam, Tetraconazole, Thiabendazole, Thiram, Triadimenol, Triazoxide, Triticonazole, Captan, Diniconazole, Myclobutanil, Tolyfluanid, a compound of formula A-1

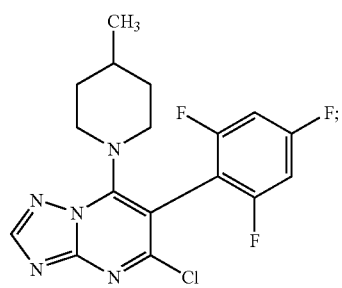
(A-1)

a compound of formula A-2

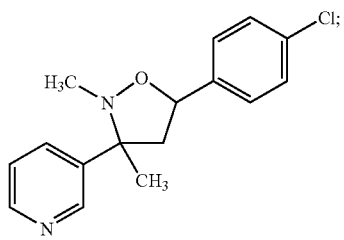
(A-2)

and a compound of formula A-3

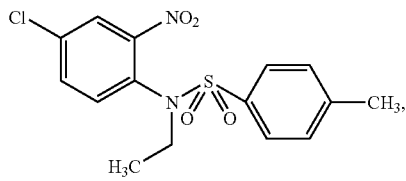
(A-3)

a compound of formula A-4

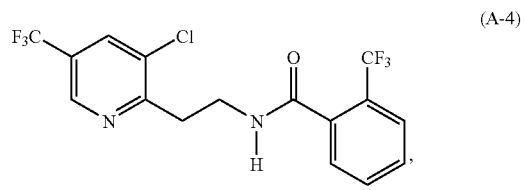
(A-4)

a compound of formula A-5

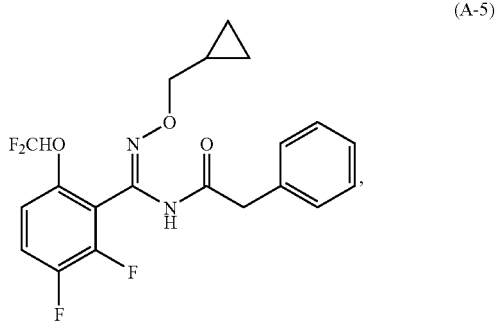
(A-5)

a compound of formula A-6

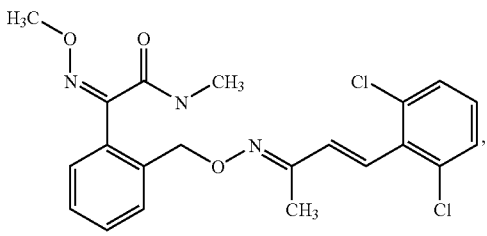
(A-6)

a compound of formula A-7

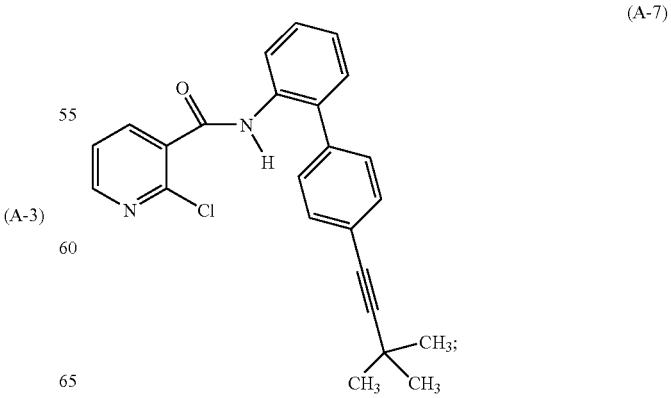
(A-7)

a compound of formula A-8
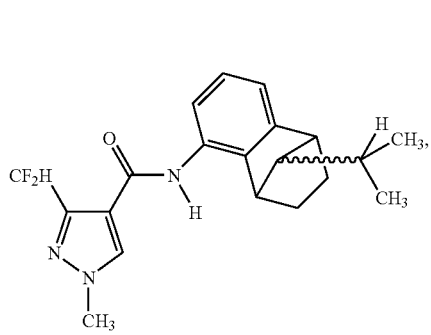
(A-8)
which represents an epimeric mixture of the racemic syn and anti compounds, wherein the ratio of racemic syn compounds to racemic anti compounds is from 1000:1 to 1:1000;
a compound of formula A-9
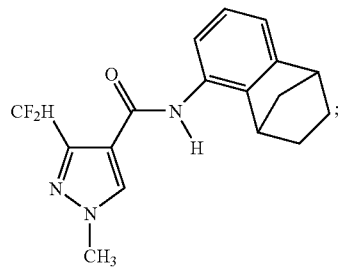
(A-9)
a compound of formula A-10
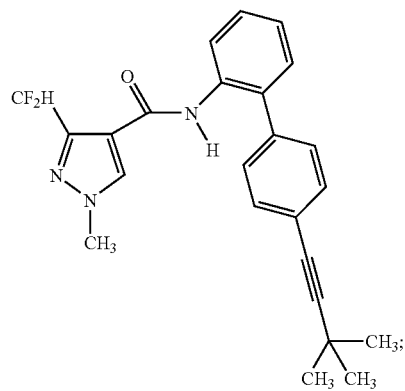
(A-10)
a compound of formula A-11
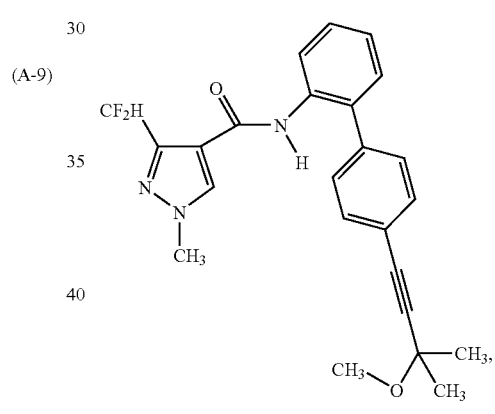
(A-11)
a compound of formula A-12
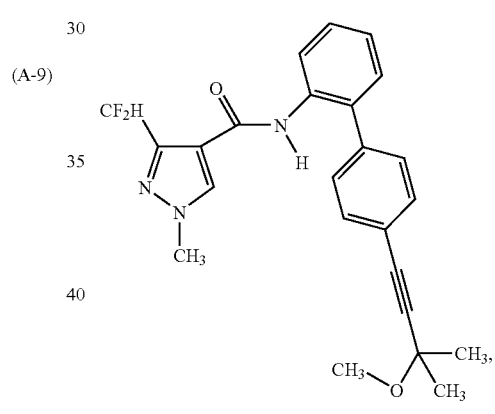
(A-12)
a compound of formula A-13
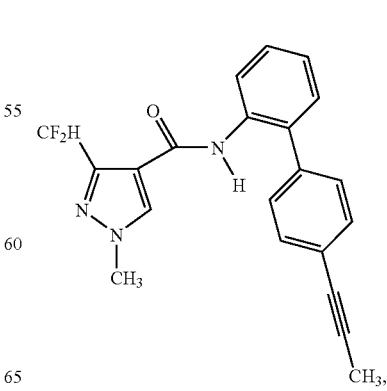
(A-13)

a compound of formula A-14

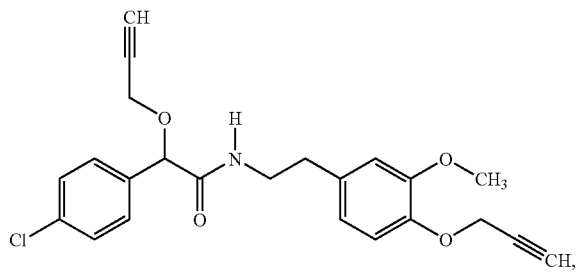

(A-14)

a compound of formula A-15

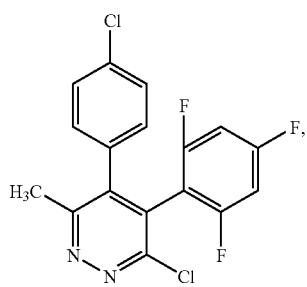

(A-15)

and a compound of formula A-16

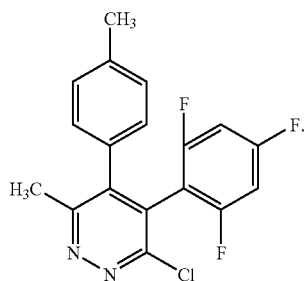

(A-16)

The compound of formula A-1 is described in WO 98/46607 and is registered under CAS-214706-53-3; the compound of formula A-2 is described in EP-1-035-122 and is registered under CAS-291771-99-8 and CAS-291771-83-0; the compound of formula A-3 is described in WO 00/065913 and is registered under CAS-304911-98-6; the compound of formula A-4 is described in WO 04/016088; the compound of formula A-5 is described in WO 99/14187 and registered under CAS: 221201-92-9; the compound of formula A-6 is registered under CAS: 366815-39-6; the compounds of formula A-7, A-8, A-9, A-10, A-11, A-12 and A-13 are all described in WO 04/058723, WO 04/035589 and WO 06/037632; the compound A-14 is described in WO 01/87822. The compounds A-15 and A-16 are described in WO 05/121104 and/or WO 06/001175.

According to the invention, "co-applied" includes all combinations of compositions according to the invention and the further fungicide; for example in a single "ready-mix" form, in a combined spray mixture composed from separate formulations, such as a "tank-mix", and in a combined use of the separate formulations when applied in a sequential manner, i.e. one after the other with a reasonably short period, such as a few hours or days. The order of application is not essential for working the present invention.

Preferred is a method of controlling diseases on useful plants caused by phytopathogens, which comprises applying to the useful plants or to the locus thereof a composition according to the invention or an aqueous spray mixture comprising the composition according to the invention.

Within this embodiment, preferred is a method of controlling diseases on barley plants caused by phytopathogens, which comprises applying to the barley plants or to the locus of the barley plants a composition according to the invention or an aqueous spray mixture comprising the composition according to the invention.

Furthermore preferred is a method of controlling diseases on useful plants caused by phytopathogens, which comprises applying to the propagation material thereof a composition according to the invention or a diluted formulation of a composition according to the invention.

Within this embodiment, "plant propagation material" preferably denotes seeds.

The compositions according to the invention or their diluted formulations are applied by treating the fungi, the useful plants, the propagation material thereof or the locus thereof with a composition according to the invention or their diluted formulation.

The composition according to the invention or their diluted formulation may be applied before ("preventive treatment") or after infection ("curative treatment") of the useful plants by the fungi.

The amount of a composition of the invention or their diluted formulation to be applied, will depend on various factors, such as the subject of the treatment, such as, for example the useful plants or soil; the type of treatment, such as, for example spraying; the purpose of the treatment, such as, for example prophylactic or therapeutic; the type of fungi to be controlled or the application time.

With the composition according to the invention it is possible to inhibit or destroy the phytopathogenic microorganisms which occur in plants or in parts of plants (fruit, blossoms, leaves, stems, tubers, roots) in different parts of the useful plants, while at the same time the parts of useful plants which grow later are also protected from attack by phytopathogenic microorganisms.

The compositions according to the invention are particularly useful for controlling the following plant diseases:
*Alternaria* species in fruit and vegetables,
*Botrytis cinerea* in strawberries, tomatoes, sunflower, pulse crops, vegetables and grapes,
*Cercospora arachidicola* in peanuts,
*Cochliobolus sativus* in cereals,
*Colletotrichum* species in pulse crops,
*Erysiphe* species in cereals,
*Erysiphe cichoracearum* and *Sphaerotheca fuliginea* in cucurbits,
*Fusarium* species in cereals and maize,
*Helminthosporium* species in maize, rice and potatoes, such as *Helminthosporium graminearum* on barley,
*Hemileia vastatrix* on coffee,
*Phakopsora* species in soybean,
*Puccinia* species in cereals, broadleaf crops and perennial plants,
*Pseudocercosporella* species in cereals,
*Podosphaera* species in fruits,
*Pyrenophora* species in barley,
*Pyricularia oryzae* in rice, Rhynchosporium species in barley and rye,
Sclerotinia species in lawns, lettuce, vegetables and oil seed rape,
Septoria species in cereals, soybean and vegetables,
Uncinula necator, Guignardia bidwellii and Phomopsis viticola in vines,
Urocystis occulta in rye,
Venturia species in fruits,
Monilinia species on fruits,
Penicillium species on citrus and apples.

When applied to the useful plants cyprodinil is applied at a rate of 10 to 2000 g cyprodinil/ha, particularly 10 to 1000 g cyprodinil/ha, most preferably 10 to 450 g cyprodinil/ha, e.g. 100, 300, 375 or 450 g cyprodinil/ha, together with 10 to 2000 g of the unsaturated $C_{18}$-fatty acid/ha, particularly 10 to 1000 g of the unsaturated $C_{18}$-fatty acid/ha, most preferably 10 to 450 g of the unsaturated $C_{18}$-fatty acid/ha, e.g. 100, 300, 375 or 450 of the unsaturated $C_{18}$-fatty acid/ha.

In agricultural practice the application rates of the composition according to the invention or their diluted formulation depend on the type of effect desired, and typically range from 20 to 4000 g of total composition per hectare.

When applied to seeds cyprodinil is applied at a rate of 0.001 to 10 g of Cyprodinil per kg of seed, preferably from 0.01 to 1 g per kg of seed, together with 0.001 to 10 g of the unsaturated $C_{18}$-fatty acid per kg of seed, preferably from 0.01 to 1 g per kg of seed.

The Examples which follow serve to illustrate the invention.

FORMULATION EXAMPLES

All percentage values in the following formulation examples are weight per volume values (w/v-values).
Oil-in-Water-Emulsion (EW)

| | |
|---|---|
| Cyprodinil | 30% |
| Oleic Acid | 30% |
| Butanol/polyoxypropylene/polyoxyethylene-copolymer | 2.4% |
| Modified polyester non-ionic surfactant | 2.4% |
| Propylene glycol | 12% |
| 1,2-benzisothiazolin-3-one | 0.2% |
| Non-ionic, dimethylpolysiloxane oil based aqueous emulsion | 0.2% |
| Water | Rest |

Emulsions of any required dilution, which can be used in plant protection, can be obtained from this concentrate by dilution with water. As "butanol/polyoxypropylene/polyoxyethylene-copolymer" can be used: "Toximul 8320"®, "WITCONOL NS-500LQ"®, "ATLAS G-5000"®, "ANTAROX B/848"® or "EMULSOGEN 3510®". As "non-ionic, dimethylpolysiloxane oil based aqueous emulsion" can be used: "Rhodorsil Antifoam 426R"®, "ANTIMOUSSOL SI LIQUID"® or "WACKER SILICONE ANTIFOAM EMULSION SLE"®. As "Modified polyester non-ionic surfactant" can be used: "Atlox 4914"®. As "1,2-benzisothiazolin-3-one" can be used: "PROXEL GXL"®.
Emulsifiable Concentrate

| | |
|---|---|
| Cyprodinil | 29% |
| Oleic Acid | 37% |
| 2-Ethylhexyl-acetate | 22% |
| castor oil/polyoxyethylene-copolymer (36 mol of ethylene oxide) | 5% |
| Calcium dodecylbenzenesulfonate | 5% |
| Tristyrenephenole/polyoxyethylene-copolymer (16 moles ethylene oxide) | 2% |

Emulsions of any required dilution, which can be used in plant protection, can be obtained from this concentrate by dilution with water. As "castor oil/polyoxyethylene-copolymer (36 mol of ethylene oxide)" can be used: "EMULSOGEN EL 360"®, "AGNIQUE CSO-30®", "ALKAMULS EL-620®", "SERVIROX OEG 59 E®" or "ADUXOL RIC-042®". As "Calcium dodecylbenzenesulfonate" can be used: "ATLOX 4838B"®, "RHODACAL 60/B-E®", "SERMUL EA 88®" or "AGNIQUE ABS 96A®". As "Tristyrenephenole/polyoxyethylene-copolymer (16 moles ethylene oxide)" can be used: "SOPROPHOR BSU"®, "AGNIQUE TSP-16®", "EMULSOGEN TS 160®" or "MAKON TSP-16®".
Suspo-Emulsion for Seed Treatment

| | |
|---|---|
| Cyprodinil | 2.5% |
| Oleic Acid | 2.5% |
| Fludioxonil | 2.6% |
| Flutriafol | 2.7% |
| Ethoxylated tristyrylphenol sulfate, ammonium salt | 2% |
| Butanol-polyoxypropylene/polyoxyethylene-copolymer | 2% |
| Sodium salt of a maleic acid polymer | 1% |
| Ethoxylated tallow alcohol (15 mol of ethylene oxide) | 2% |
| Modified polyester non-ionic surfactant | 2% |
| Water | 81.7% |

Suspo-emulsions of any required dilution, which can be used in seed treatment, can be obtained from this concentrate by dilution with water. As "ethoxylated tristyrylphenol sulfate, ammonium salt" can be used: "Soprophor 4D 384"®, "AGNIQUE TSP-16SA-B", "DISPERSOGEN GRTE" or "STEOL TSP-16 N". As "Butanol-polyoxypropylene/polyoxyethylene-copolymer" can be used: "Toximul 8320"®, "WITCONOL NS-500LQ"®, "ATLAS G-5000"®, "ANTAROX B/848"® or "EMULSOGEN 3510"®. As "Sodium salt of a maleic acid polymer" can be used: "Sokalan CP9"®. As "Modified polyester non-ionic surfactant" can be used: "Hypermer A70"®.

Example A-1

EW-Formulation 300 g cyprodinil, technical grade, is mixed with 300 g oleic acid by stirring (if necessary, the mixture can be warmed up to 40° C. to facilitate melting of cyprodinil). In another vessel, 24 g of a copolymer of butanol and polyoxypropylene/polyoxyethylene ("Toximul 8320"®, "WITCONOL NS-500LQ"®, "ATLAS G-5000®", "ANTAROX B/848®" or "EMULSOGEN 3510®" can be used), 24 g modified polyester non-ionic surfactant ("Atlox 4914"®), 120 g propylene glycol (technical), 2 g 1,2-benzisothiazolin-3-one ("Proxel GXL"®) and 2 g non-ionic, dimethylpolysiloxane oil based aqueous emulsion ("Rhodorsil Antifoam 426R"®, "ANTIMOUSSOL SI LIQUID"®, or "WACKER SILICONE ANTIFOAM EMULSION SLE®" can be used) was mixed together with water to form an aqueous solution. Then the mixture consisting of cyprodinil and oleic acid is added to the aqueous solution with high shear mixing to form an EW-formulation. The amount of total water used was enough to form 1 l of total EW-formulation.

Example A-2

EC-Formulation 30 g cyprodinil, technical grade, is mixed with 37.6 g oleic acid by stirring (if necessary, the mixture can be warmed up to 40° C. to facilitate melting of cyprodinil). 4.8 g of a condensation product of castor oil and ethylene oxide ("Emulsogen EL 360"®, "AGNIQUE CSO-30®", "ALKAMULS EL-620®", "SERVIROX OEG 59 E®" or "ADUXOL RIC-042®" can be used), 5.2 g dodecylbenzene sulfonic acid, Ca-salt, linear ("ATLOX 4838B"®, "RHODACAL 60/B-E®", "SERMUL EA 88®" or "AGNIQUE ABS 96A®" can be used) and 2 g of a condensation product of tristyrenephenole and 16 moles ethylene oxide ("SOPROPHOR BSU"®, "AGNIQUE TSP-16®", "EMULSOGEN TS 160®" or "MAKON TSP-16®" can be used) are added to the mixture. 2-Ethylhexyl-acetate is added to yield 100 ml of the final EC-formulation.

APPLICATION EXAMPLES

Example B-1

Physico-Chemical Behaviour of an Aqueous Concentrate after Prolonged Storage The following aqueous concentrates were prepared:

TABLE B-1a

| Formulation Ingredient | Aqueous concentrates | | |
|---|---|---|---|
| | Concentrate B-1 according to the invention | Concentrate C-1, conventional formulation | Concentrate C-2, conventional formulation |
| Cyprodinil | 2.5% | 2.5% | 2.5% |
| Oleic Acid | 2.5% | — | — |
| Fludioxonil | 2.6% | 2.6% | 2.6% |
| Flutriafol | 2.7% | 2.7% | 2.7% |
| Ethoxylated polyarylphenol sulfate, ammonium salt | 2% | 2% | 2% |
| Butanol-polyoxypropylene/polyoxyethylene-copolymer | 2% | 2% | — |
| Sodium salt of a maleic acid polymer | 1% | — | 2% |
| Ethoxylated tallow alcohol | 2% | — | — |
| Modified polyester non-ionic surfactant | 2% | — | — |
| Water | 81.7% | 88.2% | 88.2% |

As "ethoxylated polyarylphenol sulfate ammonium salt" can be used "Soprophor 4D 384"®, as "butanol-polyoxypropylene/polyoxyethylene-copolymer" can be used "Toximul 8320" ®, as "sodium salt of a maleic acid polymer" can be used "Sokalan CP9®", as "ethoxylated tallow alcohol" can be used "Genapol T-150®" and as "modified polyester non-ionic surfactant" can be used "Hypermer A70"®.

The concentrate B-1 according to the invention is a suspoemulsion for seed treatment (SE), the conventional concentrates C-1 and C-2 are suspension concentrates (flowables for seeds; SC/FS), which are standard formulation types for seed treatment and are very similar to formulations of the prior art, such as the commercially available flowable concentrate for seed treatment from Syngenta AG, which comprises 2.5% (w/v) cyprodinil together with 2.5% (w/v) Fludioxonil and 1% (w/v) Tebuconazole, as exemplified above. Flutriafol is a commonly used fungicide in seed treatment. Soprophor 4D 384, Toximul 8320, Sokalan CP9, Genapol T-150 and Hypermer A70 types are commonly used dispersing agents.

To assess the physico-chemical behaviour of the aqueous concentrates after prolonged storage (storage stability), the formulations were prepared according to standard formulation technology and stored under the following storage conditions: repetitive cycles of 24 hours at −10° C., rapid heating to 50° C., 24 hours at 50° C. and rapid cooling to −10° C. This cycle program was maintained over the whole length of storage time.

The sieving residue of the concentrate and the viscosity of the concentrate were measured directly after formulation and 1 month and 3 months after storage using the above-mentioned conditions.

Sieving residue is measured by passing the concentrate through a sieve with 45 µm pore size. The sieving residue is expressed as % of total weight of the concentrate. A sieving residue of below 0.02% equals to excellent storage stability, a value of 0.02-0.1% equals to acceptable storage stability and a value above 0.1% equals to poor storage stability. Concentrates with poor storage stability will usually not be accepted by the end-user. Viscosity is measured at 25° C. with a BROOKFIELD viscosimeter with spindle 2 at 30 rpm. Viscosity is expressed in mPa. A value below 400 equals to excellent viscosity, a value of 400-600 equals to acceptable viscosity and a value above 600 equals to poor viscosity. Concentrates with poor viscosity will usually not be accepted by the end-user.

TABLE B-1b

| Physico-chemical behaviour of aqueous concentrates after prolonged storage | | | |
|---|---|---|---|
| Physico-chemical parameter | B-1 | C-1 | C-2 |
| Sieving Residue directly after formulation | <0.01% | 0.01% | 0.01% |
| Sieving Residue after 1 month storage (−10° C./50° C.) | <0.01% | 0.88% | 1.93% |
| Sieving Residue after 3 months storage (−10° C./50° C.) | 0.08% | 1.71% | 2.29% |
| Viscosity directly after formulation | 581 | 404 | 420 |
| Viscosity after 1 month storage (−10° C./50° C.) | 565 | 448 | 998 |
| Viscosity after 3 months storage (−10° C./50° C.) | 575 | 920 | >1000 |

Example B-2

Control of Rhynchosporium on Barley

The following EC-formulations were prepared:

TABLE B-2a

| | EC-formulations | |
|---|---|---|
| Component | B-2 | B-3 |
| Cyprodinil (in % w/v) | 30.0 | 25.0 |
| Oleic acid (in % w/v) | 31.0 | 31.0 |
| Castor oil/polyoxyethylene-copolymer (in % w/v) | 6.0 | 6.0 |
| Calcium dodecylbenzenesulfonate (in % w/v) | 4.0 | 4.0 |
| Tristyrenephenole/polyoxyethylene-copolymer (in % w/v) | 2.0 | 2.0 |
| 2-Ethylhexyl acetate | to 1 litre | to 1 litre |

The castor oil/polyoxyethylene-copolymer had 36 mole units of ethylene oxide. The Tristyrenephenole/polyoxyethylene-copolymer had 16 mole units of ethylene oxide. The example was conducted under field conditions using accepted grower practices. The compositions according to the invention were applied to field grown plants. Barley plants, variety Optic, were planted in the field. The combinations according to the invention were applied two times, the first time between Growth Stage 32-33 and the second time between Growth Stage 39-47. Disease severity was assessed as % infected area of the flag leaf 29 days after the second application; in the untreated barley plants 23% of the flag leaf area were infected. Disease control is shown as % disease control compared to untreated barley plants. The plants were harvested at Growth Stage 89 and yields were measured. The untreated barley plants had a yield of 66 dt/ha. Yield increase is shown as % yield increase compared to untreated barley plants.

TABLE B-2b

| Control of Rhynchosporium on barley | | |
|---|---|---|
| Product | Disease control | Yield increase |
| B-2, 300 g ai/ha | 92% | 26% |
| B-3, 300 g ai/ha | 95% | 19% |

Example B-3

Physico-Chemical Behaviour of Emulsifiable Concentrate (EC) after Prolonged Storage For all physico-chemical behaviour tests of example B-3, EC according to the following specifications were prepared:

TABLE B-3a

| Formulation Ingredient | Concentrates according to the invention | Concentrates of conventional formulation |
|---|---|---|
| Cyprodinil | 250-385 g/l | 250-385 g/l |
| Oleic Acid | 250-575 g/l | — |
| Propiconazole | 62.5 g/l | 62.5 g/l |
| Ethoxylated castor oil (36 mole of ethylene oxide) | 56 g/l | 56 g/l |
| Calcium dodecyl benzene sulphonate | 24 g/l | 24 g/l |
| N-methyl-pyrrolidone | 10 g/l | 10 g/l |
| Mixture of heavy aromatic hydrocarbons; "Solvesso 200" | up to 1 litre | up to 1 litre |

Propiconazole is a fungicide; ethoxylated castor oil, calcium dodecyl benzene sulphonate, N-methyl-pyrrolidone and the mixture of heavy aromatic hydrocarbons are standard formulation components. The concentrates according to the invention and the conventionally formulated concentrates are emulsifiable concentrates (EC), which is a standard formulation type in agrochemicals. The conventional formulated concentrates are very similar to the commercially available emulsifiable concentrate "STEREO"® of the prior art, which consists per liter of 250 g cyprodinil, 62.5 g propiconazole, 56 g Ethoxylated castor oil, 24 g Calcium dodecyl benzene sulphonate and 100 g N-methyl-pyrrolidone, the remainder being the above-mentioned mixture of heavy aromatic hydrocarbons ("Solvesso 200"®).

To assess the physico-chemical behaviour of the concentrates after prolonged storage (to evaluate storage stability of the composition), 100 ml samples of the concentrates were prepared according to standard formulation technology. All ingredients were fully dissolved in the concentrate solutions directly after preparation.

a) Formulation Stability:

After preparation, all samples were seeded with a single small crystal of cyprodinil, and subsequently stored at −10° C. for a storage time of 28 and/or 41 days. Assessments were performed after seeding and after storage. "Clear liquid" describes ECs where no visible phase separation has occurred. "Turbid" describes concentrates, where only little visible phase separation has occurred and no material has precipitated. "Precipitate" describes concentrates, wherein a major phase separation has occurred and material has been lost from the liquid phase by precipitation, the amount of precipitated material is described by its volume in ml.

TABLE B-3b

| | | Formulation stability of ECs after prolonged storage at −10° C. | | | | |
|---|---|---|---|---|---|---|
| | | Concentrates according to the invention | | | Concentrates, conventional formulation | |
| | | Oleic Acid | | Linoleic Acid | | |
| Cyprodinil | 28 days | 41 days | 28 days | 41 days | 28 days | 41 days |
| 250 g/l | clear liquid | turbid | clear liquid | not tested | clear liquid | precipitate (6 ml) |
| 260 g/l | clear liquid | turbid | not tested | not tested | clear liquid | precipitate (6 ml) |
| 300 g/l | turbid | turbid | not tested | not tested | precipitate (10 ml) | precipitate (16 ml) |

TABLE B-3b-continued

Formulation stability of ECs after prolonged storage at −10° C.

| Cyprodinil | Concentrates according to the invention | | | | Concentrates, conventional formulation | |
|---|---|---|---|---|---|---|
| | Oleic Acid | | Linoleic Acid | | | |
| | 28 days | 41 days | 28 days | 41 days | 28 days | 41 days |
| 350 g/l | turbid | turbid | clear liquid | not tested | precipitate (10 ml) | precipitate (16 ml) |
| 382 g/l | turbid | not tested | clear liquid | not tested | no stable concentrate | |

In concentrates according to the invention, the unsaturated $C_{18}$-fatty acid is present in a weight ratio of cyprodinil to the unsaturated $C_{18}$-fatty acid of 44:56. In conventionally formulated concentrates, no unsaturated $C_{18}$-fatty acid is present. At a concentration of 382 g/l cyprodinil, no stable conventionally formulated concentrate could be generated. Furthermore, at a concentration of 260 g/l cyprodinil, concentrates according to the invention with weight ratios of cyprodinil to oleic acid/linoleic acid of 31:65 and 35:65 were formulated. All four concentrates were "clear liquids" after 28 days storage at −10° C. At a concentration of 300 g/l cyprodinil, a concentrate according to the invention with a weight ratio of cyprodinil to oleic acid of 55:45 was also formulated. This concentrate was a "clear liquid" after 28 days storage at −10° C.

b) Wet Sieve Residue after Aqueous Dilution:

After preparation, all samples were stored at 54° C. for a storage time of 28-41 days. The "Wet sieve residue after aqueous dilution" was analyzed prior to and after storage. To measure the wet sieve residue after aqueous dilution, water of a known hardness and ion content was poured into a 250 ml jacketed vessel and stirred continuously using a magnetic stirrer, at a speed such that a 3 cm vortex was observed. The water was cooled to 5° C., and the concentrate was then added to form a 1% dilution. The aqueous dilution of the concentrate was stirred for 2 hours at 5° C. The dilution was poured through 150 μm and 53 μm meshed sieves and the residue was dried and weighed. Wet sieve residue is expressed as percentage of the total mass of concentrate added. A wet sieve residue of below 1.0% is a characteristic of a good emulsion, a value of 1.0-5.0% is a characteristic of an acceptable emulsion and a value above 5.0% is a characteristic of a poor emulsion. A high wet sieve residue in this test indicates that such concentrates form large amounts of deposit upon preparation of spray-mixtures for foliar application by the end-user. Such large amounts of deposit may then clog the spray nozzles of the application apparatus. Therefore, such concentrates, which form large amounts of deposit due to poor storage stability, will not be accepted by the end-user.

TABLE B-3c

Wet sieve residue after aqueous dilution

| Cyprodinil | Concentrates according to the invention | | Concentrates, conventional formulation |
|---|---|---|---|
| | Oleic Acid | Linoleic Acid | |
| 250 g/l | 0.0% (0.0%)* | 0.3% (0.5%)* | 0.0% (0.0%)* |
| 300 g/l | 1.2% (1.7%)* | not tested | not tested |
| 350 g/l | 0.1% (0.5%)* | 1.6% (0.5%)* | 21.8% (10.9%)* |
| 382 g/l | 0.8% (1.8%)* | 0.7% (0.9%)* | no stable concentrate |

TABLE B-3d

Wet sieve residue after aqueous dilution

| Cyprodinil | Concentrates according to the invention with varying Cyprodinil:Oleic Acid ratios | | |
|---|---|---|---|
| | 31:69 | 35:65 | 55:45 |
| 260 g/l | 0.2% | 0.6% | not tested |
| 300 g/l | not tested | not tested | 0.9% (1.1%)* |

The value in brackets in tables B-3c and B-3d is the "wet sieve residue" measured without storage.

Table B-3c: in concentrates according to the invention, the unsaturated $C_{18}$-fatty acid is present in a weight ratio of cyprodinil to the unsaturated $C_{18}$-fatty acid of 44:56. In conventionally formulated concentrates, no unsaturated $C_{18}$-fatty acid is present.

Table B-3d: in the concentrates according to the invention, the ratios of cyprodinil to oleic acid is 31:69, 35:65 and 55:45, respectively.

c) Particle Sizes after Aqueous Dilution:

After preparation, all concentrates were stored at 54° C. for a storage time of 28-41 days. Dilutions of samples before and after were analyzed by a laser diffraction particle size analyzer. A representative sample was taken and added to water of known hardness and ion content, and dispersed at an adequate concentration to be detected by the instrument. Results are expressed as particle diameter (in μm) and are expressed as "mean particle size" and as "percentage of particles with a size of under 2 μm".

For this invention, "percentage of particles with a size of under 2 μm" is a good indicators for the performance of the composition in normal use. The particle size of the composition according to the invention will depend on the exact composition. Generally, a value of above 33% indicates that the emulsion has good droplet sizes and/or size distributions, of 20-33% acceptable droplet sizes and/or size distributions and of below 20% usually non-acceptable droplet sizes and/or size distributions.

The "mean particle size" can also be used to describe the droplet size distribution. A "mean particle size" of below 10 μm is again a characteristic of a concentrate with good droplet sizes and/or size distributions, of 10-20 μm with acceptable droplet sizes and/or size distribution and of above 20 μm with non-acceptable droplet sizes and/or size distribution. A smaller droplet size will give increased emulsion stability, and no change in droplet size post storage indicates increased storage stability.

TABLE B-3e

Particle size after aqueous dilution

| Cyprodinil | Concentrates according to the invention | | Concentrates, conventional formulation |
|---|---|---|---|
| | Oleic Acid | Linoleic Acid | |
| | % of particles <2 μm | % of particles <2 μm | % of particles <2 μm |
| 250 g/l | 30.2% (27.7%)* | 33.9% (34.3%)* | 13.0% (18.1%)* |
| 260 g/l | 28.3% (31.9%)* | 30.4% (33.4%)* | 11.0% (15.2%)* |
| 300 g/l | 33.6% (40.0%)* | 27.0% (56.5%)* | 14.9% (17.7%)* |
| 350 g/l | 35.9% (30.9%)* | 33.2% (41.0%)* | 22.5% (21.0%)* |
| 382 g/l | 33.2% (23.5%)* | 33.6% (26.9%)* | no stable concentrate |
| | Mean size | Mean size | Mean size |
| 250 g/l | 8.6 μm (8.4 μm)* | 9.2 μm (9.0 μm)* | 24.3 μm (15.4 μm)* |
| 260 g/l | 9.9 μm (7.3 μm)* | 9.6 μm (9.6 μm)* | 29.5 μm (17.6 μm)* |
| 300 g/l | 5.6 μm (4.2 μm)* | 11.3 μm (2.3 μm)* | 26.4 μm (16.1 μm)* |
| 350 g/l | 3.9 μm (4.3 μm)* | 4.7 μm (2.7 μm)* | 16.3 μm (13.4 μm)* |
| 382 g/l | 2.7 μm (10.5 μm)* | 3.4 μm (12.2 μm)* | no stable concentrate |

TABLE B-3f

Particle size after aqueous dilution

| Cyprodinil | Concentrates according to the invention with varying Cyprodinil:Oleic Acid ratios | | | Concentrates, conventional formulation |
|---|---|---|---|---|
| | 31:69 | 35:65 | 55:45 | |
| | % of particles <2 μm | % of particles <2 μm | % of particles <2 μm | % of particles <2 μm |
| 260 g/l | 33.5% (34.9%)* | 41.1% (40.7%)* | not tested | 11.0% (15.2%)* |
| 300 g/l | not tested | not tested | 34.9% (36.4%)* | 14.9% (17.7%)* |
| | Mean size | Mean size | Mean size | Mean size |
| 260 g/l | 4.5 μm (4.0 μm)* | 3.8 μm (6.0 μm)* | not tested | 29.5 μm (17.6 μm)* |
| 300 g/l | not tested | not tested | 8.0 μm (8.4 μm)* | 26.4 μm (16.1 μm)* |

The value in brackets in tables B-3e and B-3f is the "mean size" or "percentage of particles <2 μm" measured without storage Table B-3: in concentrates according to the invention, the unsaturated $C_{18}$-fatty acid is present in a weight ratio of cyprodinil to the unsaturated $C_{18}$-fatty acid of 44:56. In conventionally formulated concentrates, no unsaturated $C_{18}$-fatty acid is present.

Table B-3f: in the concentrates according to the invention, the ratios of cyprodinil to oleic acid is 31:69, 35:65 and 55:45, respectively.

Compositions of the invention surprisingly give a higher "percentage of particles<2 μm" than the conventional concentrates with a lower "mean size". In the main there was negligible change after storage in compositions according to the invention, but deterioration was seen in the conventional concentrates, showing reduced storage stability.

What is claimed is:

1. A fungicidal composition in the form of a liquid concentrate, which, in addition to at least one carrier or surfactant, comprises cyprodinil and an unsaturated $C_{18}$-fatty acid selected from oleic acid, linoleic acid and linolenic acid.

2. A composition according to claim 1, wherein the composition is substantially water-free.

3. A composition according to claim 2, wherein the composition comprises at least 26% by weight cyprodinil.

4. A composition according to claim 2, wherein the composition comprises from 26% to 53% by weight cyprodinil.

5. A composition according to claim 1, wherein the composition is an aqueous composition.

6. A composition according to claim 5, wherein the composition comprises at least 1% by weight cyprodinil.

7. A composition according to claim 5, wherein the composition comprises from 1% to 10% by weight cyprodinil.

8. A composition according to claim 1, wherein the weight ratio of cyprodinil to the unsaturated $C_{18}$-fatty acid is from 20:80 to 80:20.

9. A composition according to claim 1, wherein the weight ratio of cyprodinil to the unsaturated $C_{18}$-fatty acid is about 44:56.

10. A composition according to claim 1, wherein the composition is an emulsifiable concentrate.

11. A composition according to claim 1, wherein the composition is an emulsion.

12. An aqueous spray mixture comprising a composition according to claim 1.

13. An aqueous spray mixture according to claim 12, wherein the aqueous spray mixture comprises 0.01 to 20% by weight cyprodinil.

14. A process for the preparation of a composition according to claim 1, which comprises mixing cyprodinil with an unsaturated $C_{18}$-fatty acid and with at least one carrier or surfactant, wherein the unsaturated $C_{18}$-fatty acid is selected from oleic acid, linoleic acid and linolenic acid.

15. A mixture consisting of cyprodinil and an unsaturated $C_{18}$-fatty acid, wherein the unsaturated $C_{18}$-fatty acid is selected from oleic acid, linoleic acid and linolenic acid.

16. A mixture according to claim 15, wherein the weight ratio of cyprodinil to the unsaturated $C_{18}$-fatty acid is from 20:80 to 53:47.

17. A mixture according to claim 15, wherein the weight ratio of cyprodinil to the unsaturated $C_{18}$-fatty acid is about 44:56.

18. A method of controlling diseases on useful plants caused by phytopathogens, which comprises applying to the useful plants, propagation material thereof or to the locus of thereof a composition according to claim 1 or a diluted formulation of a composition according to claim 1.

19. A method of controlling diseases on useful plants caused by phytopathogens, which comprises applying to the useful plants or to the locus thereof a composition according to claim 1 or an aqueous spray mixture according to claim 12.

20. A method according to claim 19, wherein the useful plant is barley.

21. A method of controlling diseases on useful plants caused by phytopathogens, which comprises applying to the plant propagation material thereof a composition according to claim 1 or an aqueous spray mixture according to claim 12.

* * * * *